US006872697B2

(12) United States Patent
Blanc et al.

(10) Patent No.: US 6,872,697 B2
(45) Date of Patent: Mar. 29, 2005

(54) OXIME AS PERFUMING INGREDIENT

(75) Inventors: Pierre-Alain Blanc, Crassier (CH); Piero Fantini, Geneva (CH); Peter Fankhauser, Meyrin (CH)

(73) Assignee: Firmenich SA, Geneva (CH)

( * ) Notice: Subject to any disclaimer, the term of this patent is extended or adjusted under 35 U.S.C. 154(b) by 325 days.

(21) Appl. No.: 10/224,440

(22) Filed: Aug. 19, 2002

(65) Prior Publication Data

US 2003/0069167 A1 Apr. 10, 2003

(30) Foreign Application Priority Data

Sep. 7, 2001 (WO) ................................ PCT/IB01/01630

(51) Int. Cl.[7] .................................................. A61K 7/46
(52) U.S. Cl. ........................ 512/25; 510/101; 424/76.4; 424/65
(58) Field of Search ........................... 512/25; 510/101; 424/65, 76.4

(56) References Cited

U.S. PATENT DOCUMENTS 3,637,533 A 1/1972 Dahill, Jr. ................... 252/522
4,544,714 A 10/1985 Ochsner ..................... 252/522
5,066,641 A 11/1991 Narula et al. ................. 512/25

FOREIGN PATENT DOCUMENTS

| | | |
|---|---|---|
| EP | 0 079 537 | 5/1983 |
| GB | 1 073 849 | 6/1967 |

*Primary Examiner*—Monique T. Cole
(74) *Attorney, Agent, or Firm*—Winston & Strawn LLP

(57) ABSTRACT

The present invention relates to the use as a perfuming ingredient of 2-methyl-3-hexanone-oxime of formula (I)

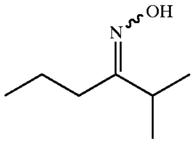

in which the wavy line represents a bond having a configuration of the type (Z) or (E) or a mixture of the two configurations.

12 Claims, No Drawings

OXIME AS PERFUMING INGREDIENT

RELATED APPLICATIONS

This application claims the priority of International Application No. PCT/IB01/01630 filed Sep. 7, 2001.

TECHNICAL FIELD

The present invention relates to the perfume industry. It concerns more particularly the use as a perfuming ingredient of 2-methyl-3-hexanone-oxime of formula

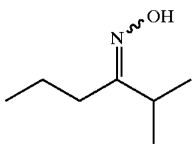

(I)

in which the wavy line represents a bond having a configuration of the type (Z) or (E) or a mixture of the two configurations.

BACKGROUND ART

To the best of our knowledge, the 2-methyl-3-hexanone-oxime is mentioned only in one prior document, namely European patent application EPA 79537. In this document, the oxime of the invention is mentioned as a chemical intermediate in the synthesis of some derivatives of the carbamoyloxime substructure. However, this prior art document does not report or suggest any organoleptic properties of the compound of formula (I), or any use of this compound in the field of perfumery.

On the other hand, U.S. Pat. No. 3,637,533 reports the use in perfumery of oximes having from 7 to 10 carbon atoms. More specifically, a number of oximes having an odor which is generally of the green, earthy, floral or yet fruity type are described. However, that patent does not disclose specifically the oxime of the invention and does not disclose or mention the specific odor properties of the 2-methyl-3-hexanone-oxime.

SUMMARY OF THE INVENTION

The invention relates to a perfuming composition or a perfumed product comprising as active ingredient 2-methyl-3-hexanone-oxime of formula (I)

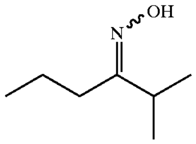

(I)

in which the wavy line represents a bond having a configuration of the type (Z) or (E) or a mixture of the two configurations, together with current perfuming coingredients, solvents or adjuvants. Preferably, this active ingredient is 2-methyl-3-hexanone oxime in the form of a mixture of isomers containing at least 65% by weight of the isomer having the (E) configuration.

The invention also relates to a method to impart, enhance or modify the odor properties of a perfuming composition or a perfumed product, which method comprises adding 2-methyl-3-hexanone-oxime of formula (I)

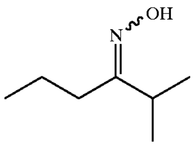

(I)

in which the wavy line represents a bond having a configuration of the type (Z) or (E) or a mixture of the two configurations as active ingredient to the composition or product. The active ingredient is added to the composition or product in an amount sufficient to impart a natural green note with a pyrazine and aldehyde connotation to the composition or product.

DETAILED DESCRIPTION OF THE PREFERRED EMBODIMENTS

Surprisingly, we have now established that 2-methyl-3-hexanone-oxime of formula

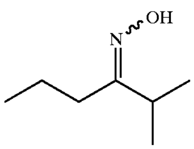

(I)

in which the wavy line represents a bond having a configuration of the type (Z) or (E) or a mixture of the two configurations, possesses specific and distinct fragrant properties, and has thus been found to be particularly useful and appreciated for the preparation of perfumes, perfuming compositions and perfumed products.

The 2-methyl-3-hexanone-oxime has an odor with a powerful and very natural green note with a pyrazine and aldehyde connotation. The overall fragrance has a pronounced odor of the leafy type, and in particular is reminiscent of hazelnut tree leaves.

Additionally, from a fragrant point of view, the use of the compound of the invention, in the form of a mixture containing at least 65% by weight of the isomer having the (E) configuration, is preferred.

The odor properties of 2-methyl-3-hexanone-oxime are all the more surprising when compared to those of the structurally related compounds disclosed in U.S. Pat. No. 3,637,533, e.g. the saturated oximes having 7 or 8 carbon atoms, which have generally an earthy or floral character. For instance, the sole $C_7$ oxime described in the U.S. patent, has a rich earthy-musty character, while the compound of the invention, also a $C_7$ oxime, has a leaves fragrance with a powerful green note.

Moreover, when compared with 3-methyl-5-heptanone-oxime, a saturated $C_8$ compound described in U.S. Pat. No. 3,637,533 as having a green-leaf odor suggestive of figue leaves, 2-methyl-3-hexanone-oxime has an odor which is less pyrazinic and with a less pronounced stem character, resulting thus in a surprisingly much stronger and natural green-leaves fragrance.

The compound of the invention is suitable for use in fine perfumery, in perfumes, colognes or after-shave lotions, as well as in other current uses in perfumery such as to perfume soaps, preparations for shower or bath mousses, oils, gels or other preparations, products such as body oils, body-care products, body deodorants and antiperspirants, hair care products such as shampoos, ambient air deodorants, or cosmetic preparations.

The compound of formula (I) can also be used in applications such as liquid or solid detergents for textile treatment, fabric softeners, or also in detergent compositions or cleaning products for cleaning dishes or varied surfaces, for industrial or household use.

In these applications, the compound according to the invention can be used alone, as well as mixed with other perfuming coingredients, solvents or additives commonly used in perfumery. The nature and variety of these co-ingredients do not require a more detailed description here, which would not be exhaustive anyway. In fact, a person skilled in the art, having a general knowledge, is able to choose them according to the nature of the product that has to be perfumed and the olfactory effect sought. These perfuming co-ingredients belong to varied chemical groups such as alcohols, aldehydes, ketones, esters, ethers, acetates, nitrites, terpenic hydrocarbons, heterocyclic nitrogen- or sulfur-containing compounds, as well as natural or synthetic essential oils. Many of these ingredients are listed in reference texts such as S. Arctander, Perfume and Flavor Chemicals, 1969, Montclair, N.J., USA, or more recent versions thereof, or in other similar books, or yet in the specialized patent literature commonly available in the art.

The proportions in which the compound according to the invention can be incorporated in the different products mentioned above vary in a broad range of values. These values depend on the nature of the product that has to be perfumed and on the olfactory effect sought, as well as on the nature of the co-ingredients in a given composition when the compound of the invention is used in admixture with perfuming co-ingredients, solvents or additives commonly used in the art.

For instance, concentrations from 0.01% to 1%, and preferably from 0.05% to 0.1%, by weight of this compound, with respect to the perfuming composition in which it is incorporated, can be typically used. Much lower concentrations than these can be used when the compound is directly applied for perfuming some of the consumer products mentioned above.

EXAMPLES

The invention will now be described in further details by way of the following examples, wherein the abbreviations have the usual meaning in the art, the temperatures are indicated in degrees centigrade (° C.); the NMR spectral data were recorded with a 360 MHz machine in $CDCl_3$, the chemical displacements δ are indicated in ppm with respect to the TMS as standard, the coupling constants J are expressed in Hz and all the abbreviations have the usual meaning in the art.

Example 1

Synthesis of 2-methyl-3-hexanone-oxime

2-Methyl-3-hexanone (228.0 g; 1.852 mol) was dissolved in 250 g of isopropyl acetate and heated to 70° C. A 50% aqueous solution of hydroxylamine (166.0 g; 2.515 mol) was added dropwise over 10 min. The mixture was heated to 80° C. After 6 hours the stirring was continued overnight at room temperature, then the aqueous phase was decanted and the organic phase washed once with brine. Drying over $Na_2SO_4$, filtration and evaporation of the solvent afforded the crude oxime. Distillation through a 10 cm Vigreux column afforded the desired oxime as a mixture of E and Z isomers (stereoisomer ratio: 71.3% E/28.7% Z, overall yield: 93.9%).

The stereoisomers (E) and (Z) have been separated by preparative GC over a SUPELCOWAX™-10, 30 m×0.53 mm, film: 2 m, column at 150° C. (retention time isomer (E)=9.3 min, retention time isomer (Z)=10.2 min).

E/Z 2-methyl-3-hexanone-oxime, mixture 71.3% E/28.7% Z

MS: (stereoisomer E): 26(1), 27(59), 28(23), 29(20), 30(8), 31(5), 37(1), 39(38), 40(9), 41(100), 42(42), 43(95), 44(14), 45(5), 46(3), 50(1), 51(3), 52(4), 53(7), 54(16), 55(20), 56(7), 57(5), 58(8), 59(2), 60(3), 65(1), 66(2), 67(5), 68(12), 69(24), 70(57), 71(4), 73(85), 74(4), 79(1), 80(1), 81(2), 82(4), 83(3), 84(8), 86(49), 87(6), 95(2), 96(2), 97(5), 98(1), 101(79), 102(5), 112(13), 114(54), 115(4), 129(42[M+]), 130(13). (stereoisomer Z): 27(55), 28(22), 29(17), 30(8), 31(5), 37(1), 39(38), 40(8), 41(100), 42(39), 43(92), 44(14), 45(5), 46(2), 50(1), 51(3), 52(3), 53(7), 54(14), 55(18), 56(7), 57(6), 58(7), 59(2), 60(3), 65(1), 66(1), 67(5), 68(11), 69(26), 70(50), 71(4), 73(76), 74(3), 79(1), 80(1), 81(2), 82(4), 83(3), 84(9), 86(61), 87(5), 95(2), 96(2), 97(6), 98(1), 101(79), 102(5), 112(11), 114(46), 115(3), 129(47[M+]), 130(8).

$^1$H-RMN: 9.48 (br s; OH, minor isomer); 9.38 (br s; OH, major isomer); 3.42 (m, 1H, J=7 Hz; minor isomer, C(2)); 2.49 (m, 1H, J=7 Hz, major isomer, C(2)); 2.30 (m, 2H, major isomer, C(4)); 2.14 (m, 2H, minor isomer, C(4)); 1.58 (m, 2H, C(5)); 1.11 (d, 6H, J=6 Hz, major isomer, C(1)); 1.08 (d, 6H, J=9 Hz, minor isomer, C(1)); 0.97 (t, 3H, J=7 Hz, major isomer, C(6)); 0.95 (t, 3H, J=7 Hz, minor isomer, C(6)).

$^{13}$C-RMN: (stereoisomer E): 165.4 (s); 33.6 (d); 28.9 (t); 20.0 (q); 19.5 (t); 14.6 (q). (stereoisomer Z): 164.9 (s); 32.2 (t); 26.4 (d); 19.6 (t); 18.9 (q); 14.1 (q).

Example 2

A cologne for men was prepared by admixing the following ingredients

| Ingredient | Parts by weight |
|---|---|
| Linalyl acetate | 250 |
| Vetyveryl acetate | 60 |
| 10%* 7-Methyl-2H,4H-1,5-benzodioxepin-3-one [1)] | 15 |
| 10%* Cardamome essential oil | 25 |
| Cedroxyde ® [2)] | 850 |
| 10%* cis-3-Hexenol | 70 |
| 2-Ethyl-4-(2,2,3-trimethyl-3-cyclopenten-1-yl)-2-buten-1-ol [3)] | 40 |
| Dihydromyrcenol | 100 |
| 10%* Dorinone ® [4)] Beta | 10 |
| 10%* Ethylamyl ketone | 10 |
| Eugenol | 55 |
| Habanolide ® [5)] | 790 |
| Iso E Super [6)] | 840 |
| Linalool | 115 |
| Lyral ® [7)] | 140 |
| 6,6-Dimethoxy-2,5,5-trimethyl-2-hexene | 30 |
| 10%* 1,3-Dimethyl-3-phenylbutyl acetate [8)] | 50 |
| γ-Nonalactone | 10 |
| 10%* γ-Octalactone | 60 |
| Rhubofix ® [9)] | 5 |
| Polysantol ® [10)] | 10 |
| 10%* Triplal ® [11)] | 30 |
| Vertofix coeur [12)] | 760 |
| beta-Ionone | 75 |
| | 4400 |

*in the dipropyleneglycol 1) origin: Firmenich SA, Geneva, Switzerland 2) (E,E)-9,10-epoxy-1,5,9-trimethyl-1,5-cyclododecadiene; origin: Firmenich SA, Geneva, Switzerland 3) origin: International Flavors & Fragrances (IFF), USA 4) (E)-1-(2,6,6-trimethyl-1-cyclohexen-1-yl)-2-buten-1-one; origin: Firmenich SA, Geneva, Switzerland 5) pentadecenolide; origin: Firmenich SA, Geneva, Switzerland -continued A cologne for men was prepared by admixing the following ingredients

| Ingredient | Parts by weight |
|---|---|

[6] 1-octahydro-2,3,8,8-tetramethyl-2-naphthalenyl)-1-ethanone; origin: IFF, USA
[7] 4-(4-hydroxy-4-methylpentyl)-3-cyclohexene-1-carbaldehyde + 3-(4-hydroxy-4-methylpentyl)-3-cyclohexene-1-carbaldehyde; origin: IFF, USA
[8] origin: Dragoco, Germany
[9] 3',4-dimethyl-tricyclo [6.2.1.0(2,7)]undec-4-ene-9-spiro-2'-oxirane; origin: Firmenich SA, Geneva, Switzerland
[10] (−)-(1'R,E)-3,3-dimethyl-5-(2',2',3'-trimethyl-3'-cyclopenten-1'-yl)-4-penten-2-ol; origin: Firmenich SA, Geneva, Switzerland
[11] 2,4-dimethyl-3-cyclohexen-1-carboxaldehyde; origin: IFF, USA
[12] mixture of 9-acetyl-8-cedrene and cedarwood sesquiterpenes; origin: IFF, USA The addition of 40 parts by weight of 2-methyl-3-hexanone-oxime imparted to the above-mentioned base composition a natural green freshness, and the marriage of the invention oxime with the β-ionone provided a violet leaves connotation to the fragrance. Moreover, 2-methyl-3-hexanone-oxime brought into the perfume a sparkling effect, making the overall fragrance more masculine.

Example 3

A perfuming composition having a "green-leaf" character was prepared by admixing the following ingredients

| Ingredient | Parts by weight |
|---|---|
| 10%* Aldehyde C 11 undecylic | 50 |
| 50%* Aldehyde muguet [1] | 200 |
| Allyl amyl glycolate | 180 |
| 4-Methylphenylacetaldehyde | 40 |
| Hawthanol ® [2] | 40 |
| 10%* Ethylamyl ketone | 60 |
| Galbanum essential oil | 40 |
| 10%* Neobutenone ® [3] | 80 |
| Phenethylol | 100 |
| cis-3-Hexenol salicylate | 1200 |
| Triplal ® [4] | 10 |
| | 2000 |

*in the dipropyleneglycol
[1] (3,7-dimethyl-6-octenyloxy)acetaldehyde; origin: IFF, USA
[2] origin: IFF, USA
[3] 1-(5,5-dimethyl-1-cyclohexen-1-yl)-4-penten-1-one; origin: Firmenich SA, Geneva, Switzerland
[4] 2,4-dimethyl-3-cyclohexen-1-carboxaldehyde; origin: IFF, USA The addition of 500 parts by weight of 2-methyl-3-hexanone-oxime to this green-pyrazinic base composition, provided a new composition having a lift and a green dimension which was more natural and leafy. When the oxime according to the present invention was replaced by 3-methyl-5-heptanone-oxime (origin, Givaudan S. A.), the green effect was clearly weaker, the leaves connotation introduced by the (Z/E) 2-methyl-3-hexanone-oxime having been lost and the composition having acquired a more pronounced galbanum connotation.

Example 4

A perfuming composition having a tomato leaves character was prepared by admixing the following ingredients

| Ingredient | Parts by weight |
|---|---|
| Styrallyl acetate | 530 |
| 10%* Cinnamic aldehyde** | 40 |
| Hexylcinnamic aldehyde | 100 |
| 10%* laevo-Carvone | 10 |
| 10%* Ethylvanilline | 20 |
| Eucalyptol | 10 |
| Eugenol | 10 |
| Galbanum essential oil | 30 |
| Hedione ® [1] | 100 |
| Isopropylquinoleine | 200 |
| Linalool | 50 |
| 0.1%* 8-Mercapto-p-3-menthanone | 20 |
| Triplal ® [2] | 50 |
| Violettyne MIP [3] | 30 |
| | 1200 |

*in the dipropyleneglycol
**50% in Eugenol
[1] methyl dihydrojasmonate; origin: Firmenich SA, Geneva, Switzerland
[2] 2,4-dimethyl-3-cyclohexen-1-carboxaldehyde; origin: IFF, USA
[3] 1,3-undecadiene-5-yne (isopropyl myristate); origin: Firmenich SA, Geneva, Switzerland The addition of 300 parts by weight of 2-methyl-3-hexanone oxime to the above-described composition imparted to the latter a tomato leaves note much more natural and with a markedly reinforced strength that in the absence of this oxime. Moreover, the 2-methyl-3-hexanone-oxime helped to marry the leather note, brought by the isopropylquinoleine, with the green notes of this composition.

What is claimed is:

1. A perfuming composition or a perfumed product comprising as active ingredient 2-methyl-3-hexanone-oxime of formula (I)

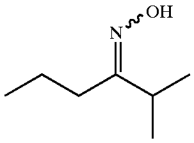

in which the wavy line represents a bond having a configuration of the type (Z) or (E) or a mixture of the two configurations, together with current perfuming coingredients, solvents or adjuvants.

2. A perfuming composition or a perfumed product according to claim 1, comprising as active ingredient 2-methyl-3-hexanone oxime in the form of a mixture of isomers containing at least 65% by weight of the isomer having the (E) configuration.

3. A perfuming composition or a perfumed product according to claim 1, in the form of a perfume, cologne or after-shave lotion, a perfumed soap, a shower or bath mousse, oil or gel, a hair care product, a shampoo, a body deodorant or antiperspirant, an ambient air deodorant, a liquid or solid detergent for textile treatment, a detergent composition or a cleaning product for dishes or varied surfaces, a fabric softener or a cosmetic preparation.

4. A perfuming composition or a perfumed product according to claim 3, wherein the active ingredient is 2-methyl-3-hexanone oxime in the form of a mixture of isomers containing at least 65% by weight of the isomer having the (E) configuration.

5. A method to impart, enhance or modify the odor properties of a perfuming composition or a perfumed product, which method comprises adding 2-methyl-3-hexanone-oxime of formula (I)

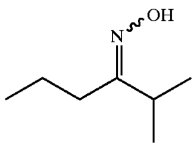

in which the wavy line represents a bond having a configuration of the type (Z) or (E) or a mixture of the two configurations as active ingredient to the composition or product.

6. The method of claim 5, wherein the active ingredient is 2-methyl-3-hexanone oxime in the form of a mixture of isomers containing at least 65% by weight of the isomer having the (E) configuration.

7. A method to impart, enhance or modify the odor properties of a perfuming composition or a perfumed product, which method comprises adding 2-methyl-3-hexanone-oxime of formula (I)

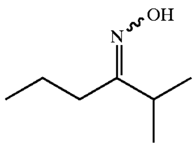

in which the wavy line represents a bond having a configuration of the type (Z) or (E) or a mixture of the two configurations, as active ingredient to the composition or product in an amount sufficient to impart a natural green note with a pyrazine and aldehyde connotation to the composition or product.

8. The method of claim 7, wherein the active ingredient is 2-methyl-3-hexanone oxime in the form of a mixture of isomers containing at least 65% by weight of the isomer having the (E) configuration.

9. A perfuming composition or a perfumed product, which comprises, as an active perfuming ingredient, 2-methyl-3-hexanone-oxime of formula (I)

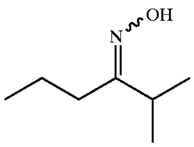

in which the wavy line represents a bond having a configuration of the type (Z) or (E) or a mixture of the two configurations, wherein the active ingredient is present in an amount sufficient to impart a natural green note with a pyrazine and aldehyde connotation to the composition or product.

10. The composition or product of claim 9, wherein the active ingredient is 2-methyl-3-hexanone oxime in the form of a mixture of isomers containing at least 65% by weight of the isomer having the (E) configuration.

11. The composition or product of claim 9, wherein the active ingredient is present together with current perfuming coingredients, solvents or adjuvants.

12. The composition or product of claim 9, in the form of a perfume, cologne or after-shave lotion, a perfumed soap, a shower or bath mousse, oil or gel, a hair care product, a shampoo, a body deodorant or antiperspirant, an ambient air deodorant, a liquid or solid detergent for textile treatment, a detergent composition or a cleaning product for dishes or varied surfaces, a fabric softener or a cosmetic preparation.

* * * * *